(12) United States Patent
Demarest et al.

(10) Patent No.: US 6,264,456 B1
(45) Date of Patent: *Jul. 24, 2001

(54) SUTURE CUTTING SYSTEM

(76) Inventors: David Demarest, 709 S. Beverwyck Rd., Parsippany, NJ (US) 07054; Timothy Lenihan, 213 Valerie Rd., Morrisville, PA (US) 19067; William Rattan, 19622 Miguel Ave., Cerritos, CA (US) 90701

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/512,962

(22) Filed: Aug. 9, 1995

Related U.S. Application Data

(62) Division of application No. 08/181,595, filed on Jan. 13, 1994, now abandoned.

(51) Int. Cl.[7] .............................. B26D 7/01; B21D 39/00

(52) U.S. Cl. ..................... 425/142; 425/289; 29/564.6; 83/100; 83/153; 83/175; 83/277; 83/279; 83/385; 83/451; 83/452; 83/454; 83/636; 83/950

(58) Field of Search ............................. 83/15, 16, 153, 83/170, 277, 466, 907, 950, 14, 18, 23, 100, 240, 451; 29/564.6, 243.517, 516, 517; 163/1, 5; 226/104, 106, 158, 162, 167, 92; 606/224–227

(56) References Cited

U.S. PATENT DOCUMENTS

| 3,611,551 | 10/1971 | Shave et al. ................. 606/226 X |
| 3,811,244 | * 5/1974 | Killen et al. ..................... 53/116 |
| 3,857,313 | * 12/1974 | Endo ................................. 83/277 |
| 3,972,214 | * 8/1976 | Jagersberger ................. 83/907 X |
| 3,980,177 | 9/1976 | McGregor .................... 606/226 X |
| 4,072,041 | 2/1978 | Hoffman et al. ............... 163/1 X |

(List continued on next page.)

FOREIGN PATENT DOCUMENTS

| 428 253 | * 5/1991 | (EP) . |
| 2 400 984 | * 4/1979 | (FR) . |

Primary Examiner—Clark F. Dexter
(74) Attorney, Agent, or Firm—Scully Scotty Murphy & Presser

(57) ABSTRACT

An apparatus for cutting an indefinite length suture strand to uniform lengths for subsequent threading and swaging to a surgical needle includes a drawing tower having at least one guide member defining a drawing axis parallel thereto. First and second gripping devices are provided to grip the indefinite length suture strand and draw it along the drawing axis; each gripping device mounted for reciprocal movement on at least one guide member. A retractable cutter for cutting the indefinite length suture strand is also provided for cutting the strand at a start position along the drawing axis. The indefinite length suture strand is fed to the drawing axis and drawn a predetermined distance beyond the location of the retractable cutter for positioning within a suture receiving opening formed in the surgical needle, while the second gripping device reciprocates to a start position along the drawing axis. The indefinite length suture strand is then inserted within the suture receiving opening of the needle and cut to a predetermined length by the retractable cutter after the second gripping means has gripped the indefinite length suture strand at the start position.

33 Claims, 8 Drawing Sheets

U.S. PATENT DOCUMENTS

| | | | |
|---|---|---|---|
| 4,318,762 | * | 3/1982 | Meyer ................................ 83/277 X |
| 4,358,976 | * | 11/1982 | Alviti ................................ 83/277 X |
| 4,672,871 | * | 6/1987 | Gudmestad ........................ 83/153 X |
| 4,722,384 | | 2/1988 | Matsutani ................................ 163/1 |
| 4,806,737 | | 2/1989 | Coates ................................ 219/390 |
| 4,832,025 | | 5/1989 | Coates ................................ 606/224 |
| 4,922,904 | | 5/1990 | Uetake et al. ........................ 606/226 |
| 4,942,796 | * | 7/1990 | Dom et al. ........................ 83/277 X |
| 5,226,336 | | 7/1993 | Coates ................................ 83/170 |
| 5,438,746 | * | 8/1995 | Demarest et al. .................... 163/1 X |
| 5,452,636 | * | 9/1995 | Rattan ................................ 83/950 X |
| 5,473,810 | * | 12/1995 | Demarest et al. ................. 83/950 X |
| 5,477,609 | * | 12/1995 | Demarest et al. ................. 83/950 X |
| 5,485,668 | * | 1/1996 | Demarest et al. ................. 83/950 X |
| 5,487,216 | * | 1/1996 | Demarest et al. ................. 83/950 X |

\* cited by examiner

SUTURE CUTTING SYSTEM

This is a divisional of application Ser. No. 08/181,595, filed on Jan. 13, 1994 now abandoned.

FIELD OF THE INVENTION

The present invention relates generally to an apparatus for cutting predetermined lengths of a flexible material such as thread, rope, wire, tubing, and the like, and more specifically, to an apparatus for automatically cutting a predetermined length of suture material for attachment to a surgical needle.

DESCRIPTION OF THE PRIOR ART

The medical products industry presently utilizes semi-automated procedures for swaging sutures to surgical needles. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to change the rack each time a different length of suture is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is additionally fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

It would be far more desirable to provide a suture cutting system and apparatus that is fully automated and which can automatically cut uniform lengths of suture material at high-speeds.

It would also be highly desirable to provide a suture cutting system that can accurately position suture material within the confines of the crimping ends of surgical needles at an appreciable rate and without elaborate techniques or manual procedures.

Also desirable would be to provide a suture cutting system that is operable under the control of a control system computer which can impart automatic adjustments to the swage tooling dies when different size sutures are swaged to various sized surgical needles.

SUMMARY OF THE INVENTION

Accordingly, it is an object of the instant invention to provide an automatic suture cutting assembly that virtually eliminates operator exposure to repetitive manual operations.

Another object of the instant invention is to provide a suture cutting apparatus that is fully automated and which can automatically and cleanly cut uniform lengths of suture material at high-speeds and without brooming of the suture tip.

It is another object of the instant invention to provide a suture cutting apparatus that includes a heat treating (tipping) device for stiffening a portion of the suture strand to be cut to aid in its insertion within a suture receiving end of a surgical needle.

Still another object of the instant invention is to provide a cutting apparatus which can be automatically set up to cut predetermined lengths of flexible articles or strands.

Yet another object of the present invention is to provide a suture cutting system that can accurately position suture material within the confines of a suture receiving opening of a surgical needle at an appreciable rate and without manual intervention.

These and other objects of the present invention are attained with an apparatus for cutting an indefinite length suture strand to uniform lengths for subsequent threading and swaging to a surgical needle having a suture receiving opening formed therein, wherein the apparatus comprises a drawing frame having at least one longitudinal member and defining a drawing axis parallel thereto. A means for feeding the indefinite length suture strand to the drawing axis for drawing and cutting thereof is provided. First and second gripping means are provided for gripping the indefinite length suture strand and drawing it along the drawing axis; the first gripping means being mounted for reciprocal movement on the longitudinal member. Also provided is a retractable cutting means for cutting the indefinite length suture strand to obtain a clean and broom-free horizontal cut. The second gripping means reciprocates to a start position along the drawing axis while the first gripping means is drawing the indefinite length suture strand to a predetermined distance beyond the retractable cutting means. The indefinite length suture strand is then inserted within the suture receiving opening of the needle and cut to a predetermined length by the retractable cutting means after the second gripping means has gripped the indefinite length suture strand at the start position.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 2(*b*) is a detailed side view of the cutting assembly taken along line 2(*b*)—2(*b*) of FIG. 2(*a*) showing the pulley assembly for moving tip and cut assembly 100 of the instant invention.

DETAILED DESCRIPTION OF THE PREFERRED EMBODIMENT

Figure 1:
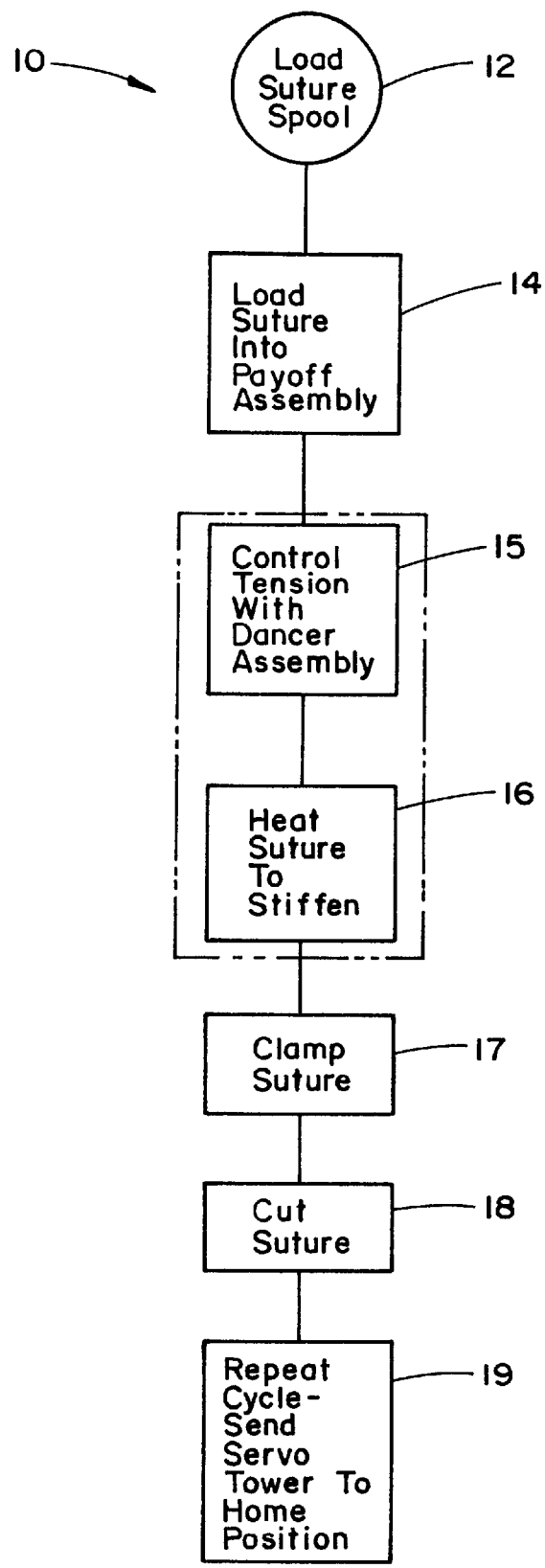
FIG. 1 is a block diagram showing the process used in the instant invention for cutting a length of material.

FIG. 1 is a block diagram generally illustrating the process 10 used to feed and cut predetermined uniform lengths of material. It should be understood that flexible materials such as thread, tubing, rope or wire of any gauge may be cut using the apparatus of the instant invention. The preferred embodiment of the instant invention is intended for use in cutting uniform lengths of suture material to enable automatic swaging of the cut suture to a surgical needle. A more detailed description of the needle threading and swaging system and the swaging station itself can be found in respective copending patent applications Ser. No. 08/181,598, now U.S. Pat. No. 5,438,746 and Ser. No. 08/181,599 assigned to the same assignee of the present invention. For descriptive purposes, the preferred embodiment discussed below is intended for cutting suture material used by medical personnel in hospitals and doctors' offices.

Generally, in the automatic cutting process 10 shown in FIG. 1, the suture material is supplied in various spools and configurations that may carry up to 5000 yards of material. This is indicated as step 12 in Fig. 1. Next, at step 14, the suture material is loaded into a payoff assembly which is part of a drawing tower apparatus to be described in detail below. This payoff assembly feeds the suture material from the spool to enable cutting thereof. When larger spools of material are used, the material may be optionally loaded in a driven spool feed assembly with a dancer as indicated at step 15 to ensure that the material does not break or snap when in tension.

Some material used in this apparatus may require extra treatment or processing. For instance, as described in detail below, it may be desirable to heat the suture material under tension at the suture tip in order to stiffen the material to facilitate the positioning thereof within the suture receiving opening of a surgical needle. Thus, at optional step 16, heat may be applied at specific points along the length of suture material. At step 17 of the block diagram of FIG. 1, the suture material is held by a bottom movable gripper located at a lower portion of the drawing tower to maintain control of the indefinite length strand of material after the suture material above it is cut off as indicated at step 18. In the subsequent cycle, this lower gripper reciprocates to an upper position of the drawing tower while drawing the suture material, while the top gripper descends, and the cycle is repeated as indicated as step 19 in FIG. 1. The process of advancing suture material 55 by alternating grippers at each cycle eliminates the recycle or return time for returning the gripper to the original position. This makes faster machine speeds and hence, higher production rates possible. A detailed explanation of the apparatus used to carry out each step will be explained in further detail hereinbelow.

Figure 2A:
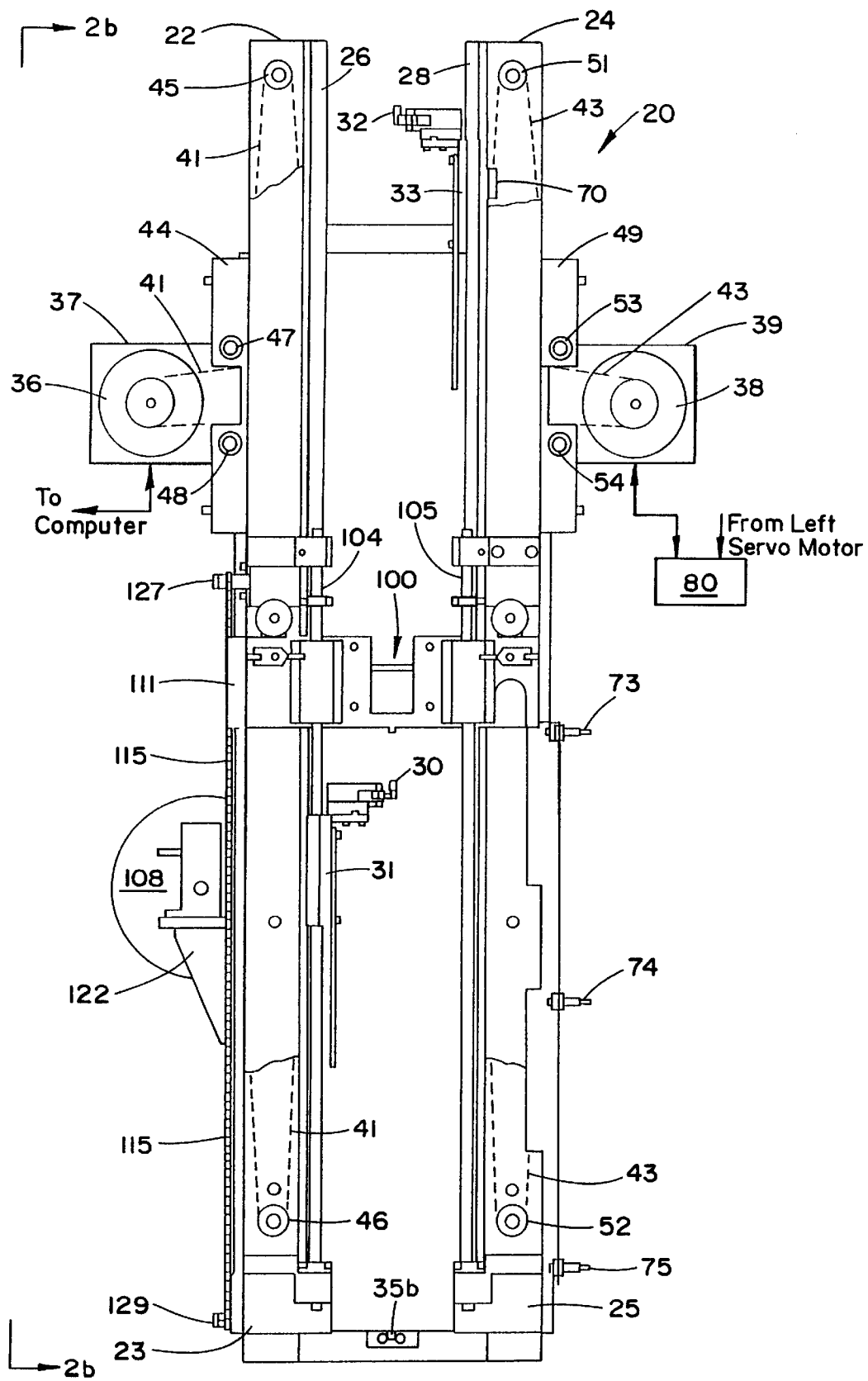
FIG. 2(*a*) is a detailed view of the cutting assembly tower of the instant invention.
Figure 5:
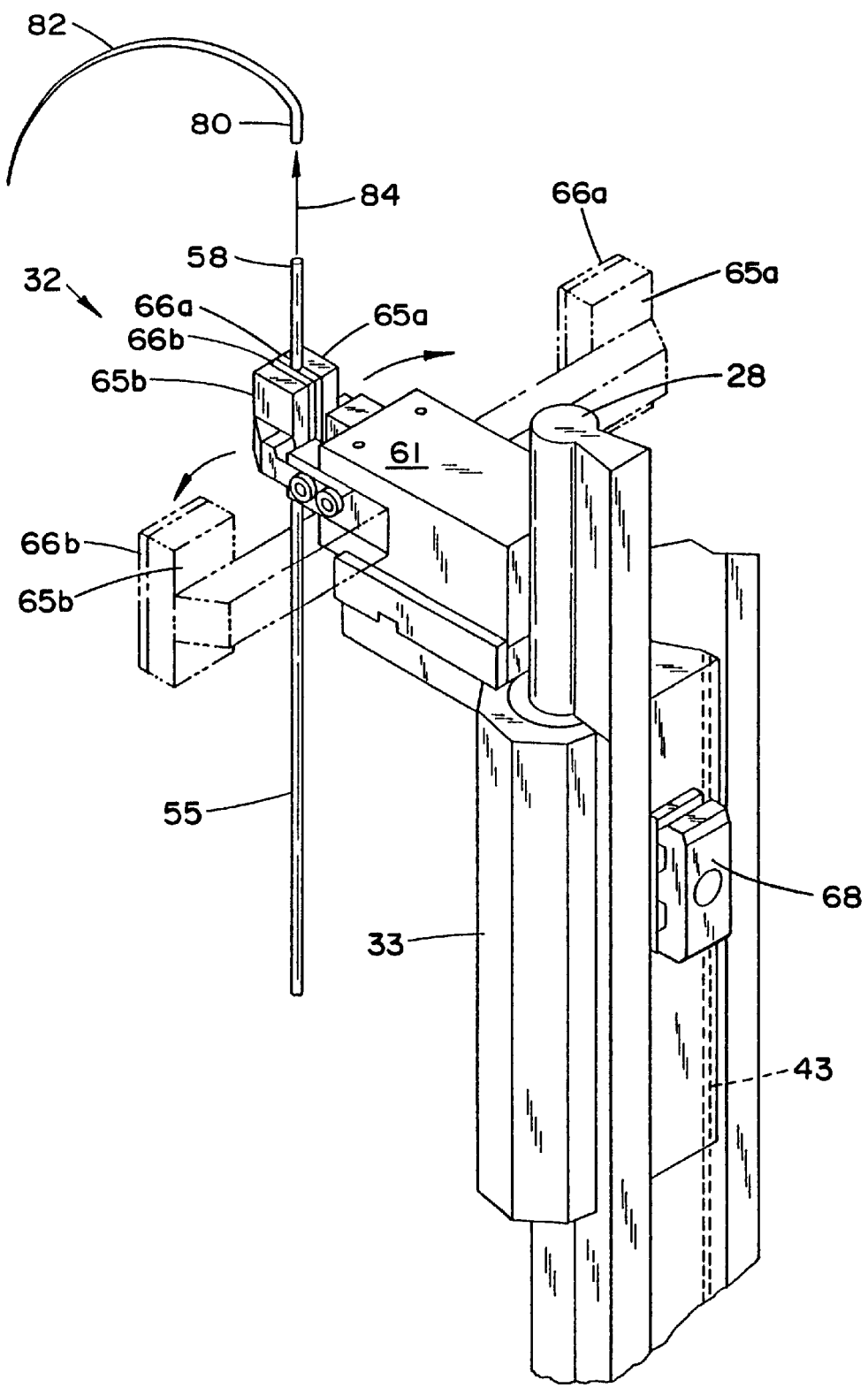
FIG. 5 is an enlarged view of a gripper assembly having gripper arms shown in their closed (suture gripping) and open positions.

The first step of the automatic cutting process 10 involves feeding the indefinite length suture material at one end of the payoff assembly. In the preferred embodiment, the payoff assembly is embodied as a drawing tower 20 shown in FIG. 2(a). The drawing tower 20 comprises left side rail 22 mounted on suitable left mounting block 23 and right side rail 24 mounted on suitable right mounting block 25 and defining a drawing frame for drawing an indefinite length of suture material along a drawing axis therebetween. Located parallel to the left and right side rails 22,24 and suitably connected thereto are respective left guide rod 26 and right guide rod 28. The first gripper means or right gripper 32 reciprocates up and down along right guide rod 28 while the second gripper means or left gripper 30 reciprocates up and down the left guide rod 26. Each of the grippers 30,32, as will be explained below, grip the suture material that is drawn from a spool through pulley 35b located at the bottom of the drawing tower 20, and carries the material to the upper end of the tower. The right gripper 32 is mounted on right gripper carrier 33 for vertical movement along right guide rod 28, and the left gripper 30 is mounted on left gripper carrier 31 for vertical movement along left guide rod 26 as shown in FIG. 2(a). FIG. 5 illustrates a gripper 32 (similar to 30) having a gripper arm drive 61 that is pneumatically operated to drive a pair of retractable gripper arms 65a, 65b toward each other to a suture gripping position, or, away from each other to an open position. Each retractable gripper arm is provided with a non-metallic pad 66a, 66b for gripping the tipped end 58 of the suture material 55 at an end thereof when actuated to the gripping position. To release the grip of the suture, gripper arms 65a, 65b are retracted approximately 180 degrees apart in the direction indicated by the arrows of FIG. 5 to the open position. When in the open position the gripper arms 65a, 65b do not interfere with the motion of the other vertically moving gripper as it reciprocates along the respective left or right rod carrying the next strand of suture material, nor will it interfere with the cutter assembly 200 as will be explained below. The retractable nature of the grippers and of the cutting assembly (discussed hereinbelow) enables single drawing axis operation.

As mentioned above, each gripper carrier and gripper thereof is designed to advance vertically along the respective left and right rods. As shown in FIG. 2(a), the right gripper 32 and gripper carrier 33 are driven by right servo motor 38 which is mounted to the right side rail 24 by right motor mounting bracket 39. Similarly, the left gripper 30 and gripper carrier 31 are driven by left servo motor 36 which is mounted to the left side rail 22 by left motor mounting bracket 37. In the preferred embodiment, both left and right servo motors are interfaced with and controlled by a control system computer, indicated generally as numeral 80 in FIG. 2(a), and as explained in further detail in copending patent application Ser. No. 08/181,607 assigned to the same assignee of the present invention. As shown in FIG. 2(a), right servo motor 38 drives timing belt 43 which consequently enables vertical positioning of right gripper carrier 33 along right rod 28, while the left servo motor 36 drives timing belt 41 which consequently enables vertical positioning of left gripper carrier 31 along left rod 26. As FIG. 5 illustrates, timing belt 43 is clamped to its respective gripper carrier 33 by a timing belt clamp 68 located on the back of the gripper carrier. A similar timing belt clamp (not shown) is provided on gripper carrier 31 for clamping timing belt 41 to enable vertical movement of gripper 30. FIG. 2(a) shows timing belt 41 engaging upper left pulley 45 and lower left pulley 46 as well as idler pulleys 47,48 which are part of tensioner block 44 that adjusts the tension of the timing belt 41 and consequently of left gripper carrier 31. Likewise, FIG. 2(*a*) shows timing belt 43 engaging upper right pulley 51 and lower right pulley 52 as well as idler pulleys 53,54 which are part of tensioner block 49 that adjusts the tension of the timing belt 43 and consequently of right gripper carrier 33.

Figure 3:
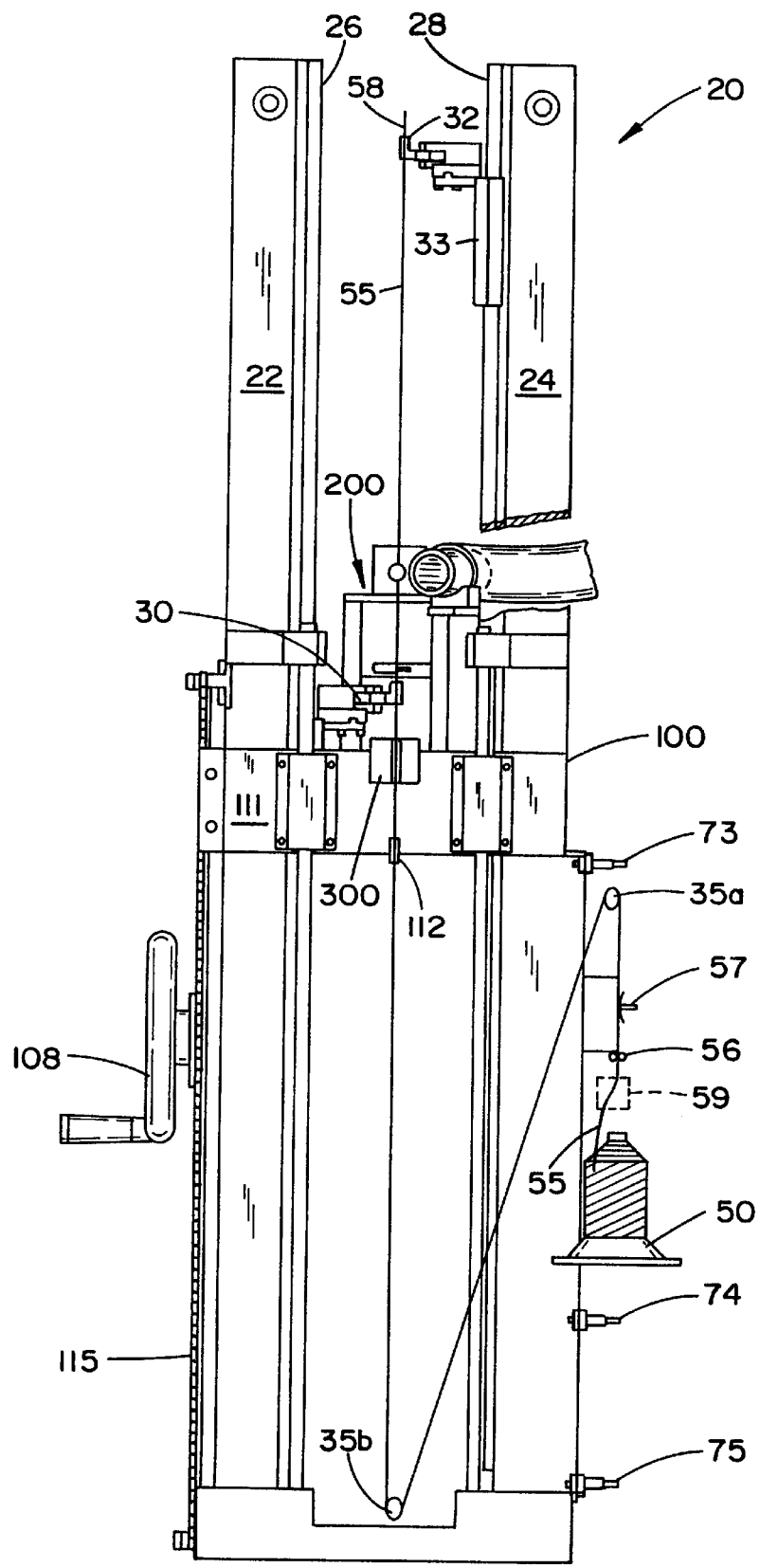
FIG. 3 is a detailed view of the servo tower 20 illustrating cutter assembly 200 mounted on tip and cut carrier 100, and the king spool supplying the suture strand.

FIG. 3 shows suture material 55 being pulled by right gripper 32 from a king spool 50. In an alternative embodiment, the spool may be motor driven in which case a dancer assembly 59 may be provided to control the tension of the material as it is being fed. To feed the indefinite length suture material to the drawing tower, the suture material 55 is first threaded through eyelet 56 to an optional knot detector 57 which senses any sudden change in the thickness of the suture material. Detection of a knot in material 55 will trigger the control system 80 to discard the cut strand of material at a subsequent operation. The suture material 55 is then advanced through the knot detector, over pulleys 35*a* and 35*b* located at the bottom of the drawing tower 20, and around pulley 112 which is mounted on the lower portion of tip and cut carrier 100 that is illustrated near the center of the tower in FIG. 3. As will be explained in detail below, and as illustrated in FIG. 3, the right gripper 32 is gripping the suture material 55 at a tipped portion of the free end 58.

Figure 2B:
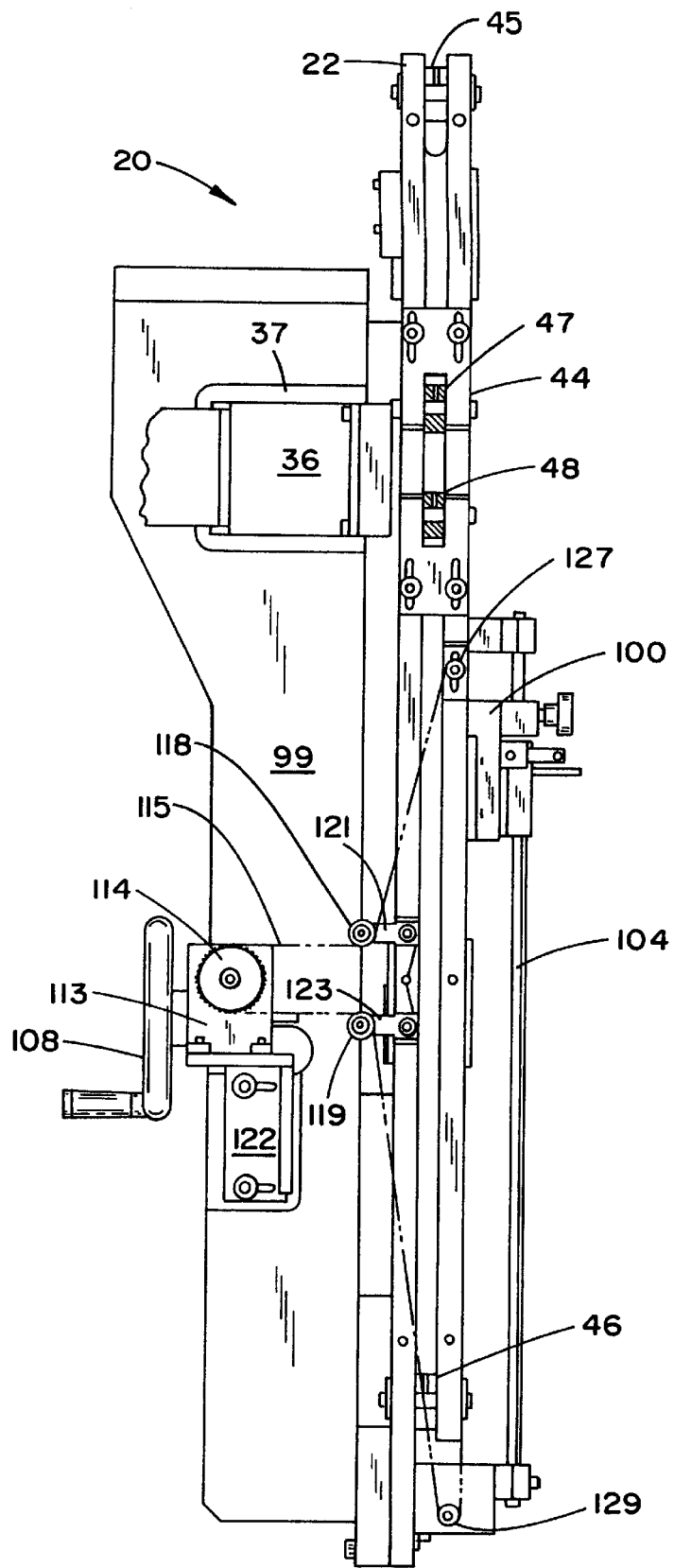
Figure 4:
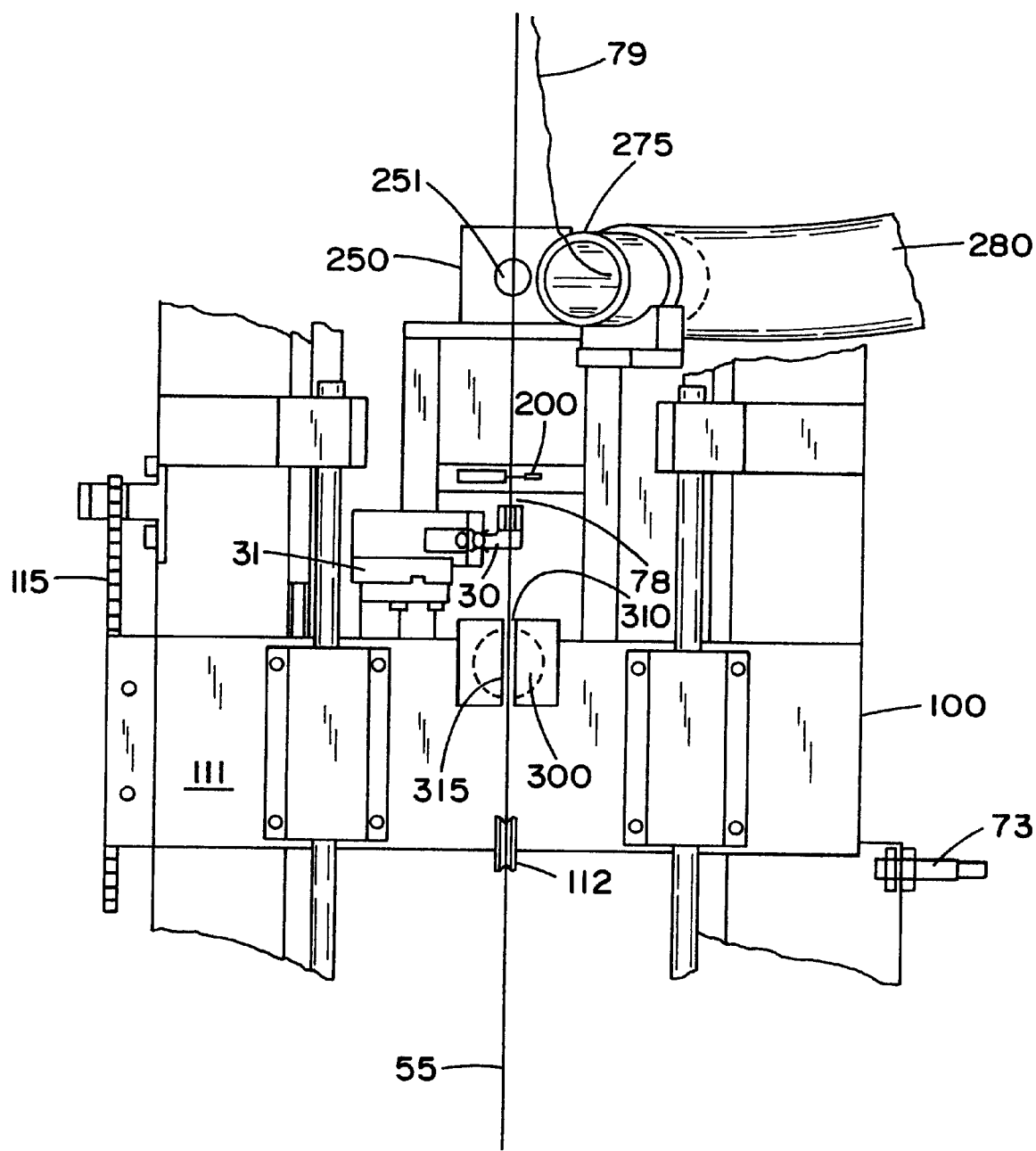
FIG. 4 is a detailed view of the tip and cut carrier 100 of the instant invention illustrating vacuum assembly 250 and tipping assembly 300 mounted thereon.
Figure 6:
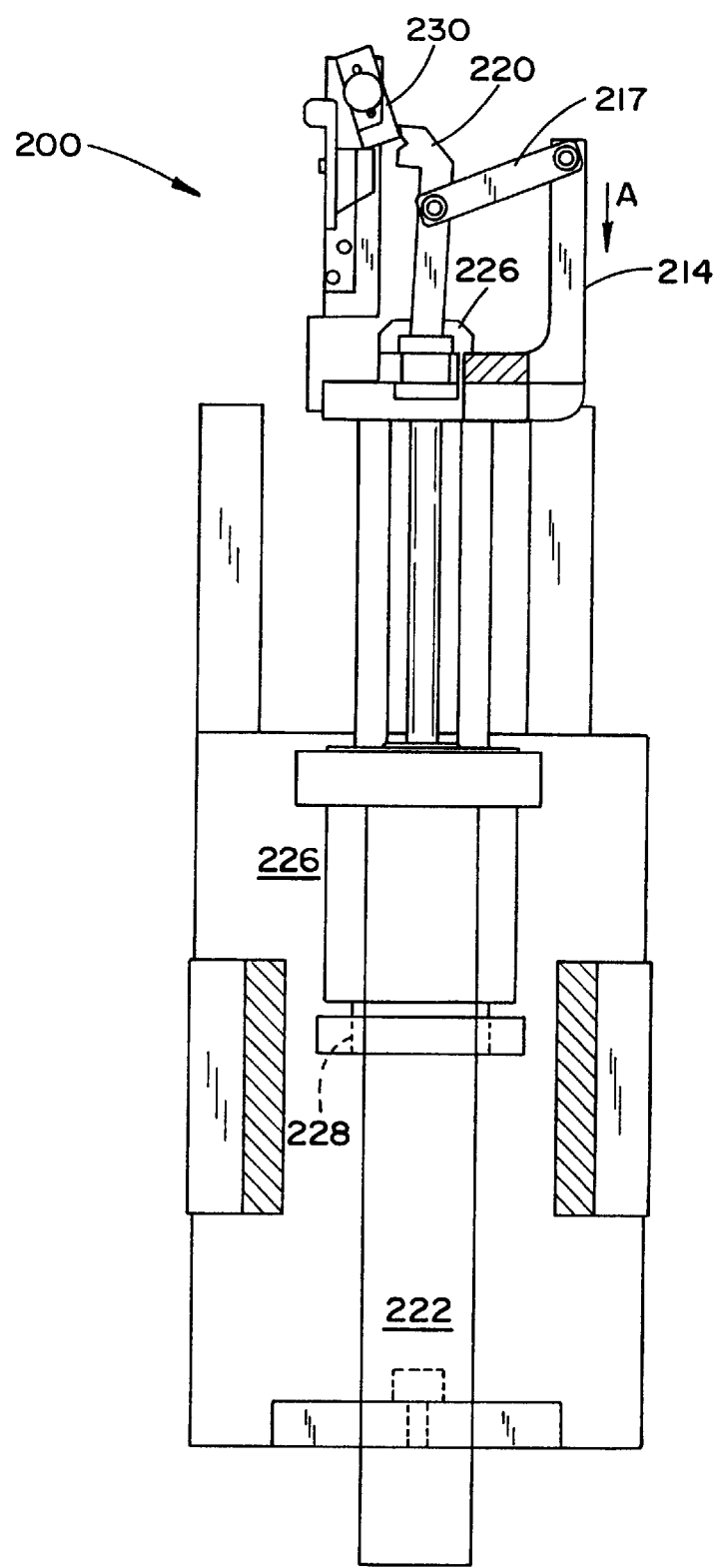
FIG. 6 is a detailed top view of the cutter assembly 200 for cutting material in the instant invention.
Figure 7:
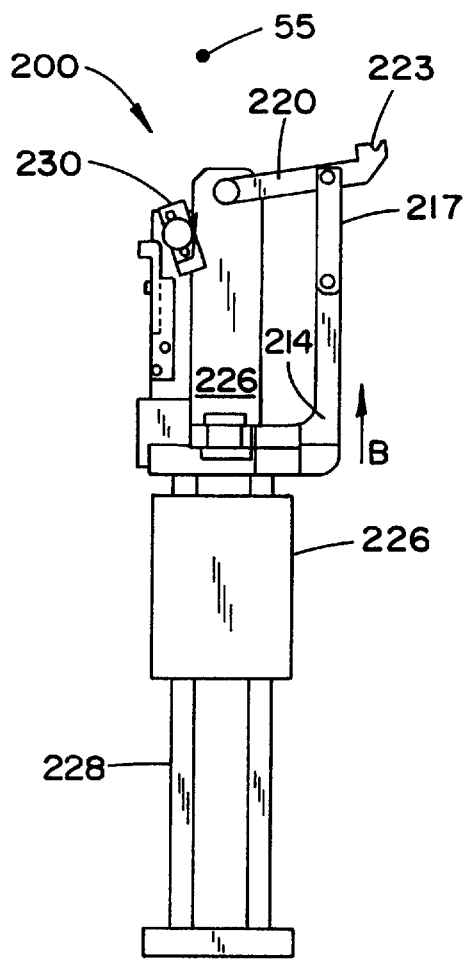
FIG. 7 is a detailed top view of the cutter assembly 200 shown in a fully retracted position.
Figure 8:
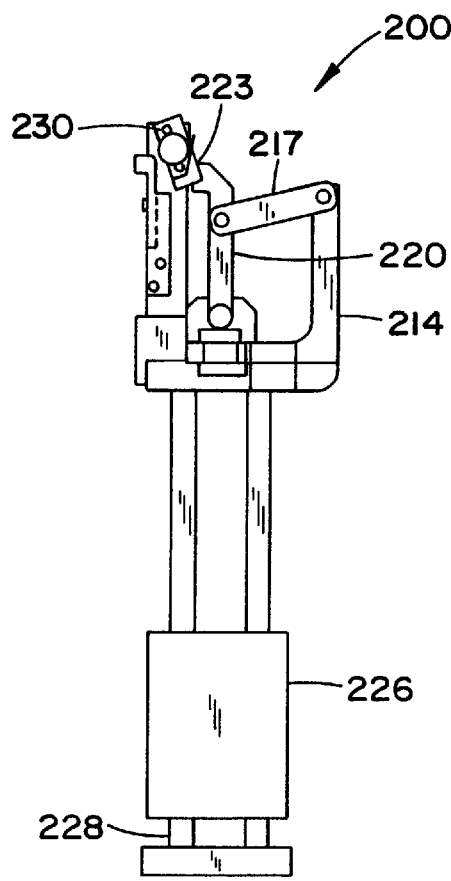
FIG. 8 is a detailed top view of the cutter assembly 200 shown in a fully extended (cutting) position.

As shown generally in FIGS. 3 and 4, tip and cut carrier 100 provides the support for tipping assembly 300 that applies heat to a specific location of the suture material, and also provides support for the cutter assembly 200 that cuts the suture material, as discussed in further detail with respect to FIGS. 6–8. FIG. 2(*a*) shows the tip and cut carrier 100 positioned along shafts 104 and 105 which are located parallel to respective left and right rods 26,28. In the preferred embodiment, vertical movement of the tip and cut carrier 100 is accomplished by cranking handwheel 108 shown in FIG. 2(*b*). Other embodiments may implement a computer controlled servo motor to vertically register the tip and cut carrier 100 prior to cutting the material. In the operation of the apparatus, both the stroke of the grippers 30,32 and the positioning of the tip and cut carrier 100 along drawing tower 20 dictates the length of the material that will be cut.

As illustrated in FIG. 2(*b*), cranking handwheel 108 actuates a gearbox 113 that rotates chain drive sprocket 114. The gearbox 113 is mounted on a gearbox mounting bracket 122 which, in turn, is mounted to frame member 99. A cable chain 115 is engaged with chain drive sprocket 114 to actuate movement of the tip and cut carrier 100 as shown in FIG. 2(*b*). The cable chain 115 also engages chain idler sprockets 118 and 119 which are rotatably mounted to upper tensioner pulley bracket 121 and lower tensioner pulley bracket 123, respectively. The vertical positioning of tensioner pulley brackets 121,123 may be adjusted to vary the slack in cable chain 115. Cable chain 115 also engages chain idler sprockets 127 and 129 which are suitably mounted on left side rail 22. As shown in FIG. 3, the back 111 of tip and cut carrier 100 is clamped to cable chain 115.

As previously mentioned, tip and cut carrier 100 includes guide pulley 112 that positions the suture material 55. The suture material is received under tension from guide pulleys 35*a*, 35*b*. As can be seen in FIG. 3, the lower threading pulley 35*b*, guide pulley 112, left gripper 30 and right gripper 32 are vertically aligned so that the cutter assembly 200 will always cut horizontally across the strand of material as will be explained below.

FIGS. 6–8 illustrate in detail the cutter assembly 200 which is suitably mounted to the tip and cut assembly 100 as shown in FIG. 4. As shown in FIG. 7, the cutter assembly comprises overcenter linkage 214 having a link arm 217 pivotally connected at one end thereof. A pivotal locator arm 220 is fixedly connected to link arm 217 at a second end thereof and is illustrated in FIG. 7 as substantially transverse thereto. The other end of locator arm 220 is pivotally connected to a stationary guide mechanism 226. Note, that all linkages described herein are simple pin linkages, the actuation of which creates the dwell moment for cutting the suture strand and obviates the need for complicated cams, slots, and sliding mechanisms.

As shown in FIG. 7, the stationary guide 226 is located in a plane perpendicular to the drawing axis of the suspended strand of material 55, and is located a distance from the strand approximately equivalent to the length of locator arm 220. In addition, overcenter linkage 214, locator arm 220, and cutting blade 230 all lie in planes perpendicular to the drawing axis of the strand of material 55.

A retractable ball slide 228 is mounted on the stationary guide 226 and coupled to overcenter linkage 214 for moving the overcenter linkage 214 and blade 230 along the stationary guide 226 in the direction indicated by arrow "A" in FIG. 6 from a cutting position to a retracted position shown in FIG. 7. As the ball slide 228 is actuated to move overcenter linkage 214 to a retracted position, the locator arm 220 is pivoted away from the strand 55 and the blade 230 is retracted. Thus, when the cutter assembly 200 is in the retracted position prior to cutting of the strand and immediately thereafter, the blade 230 and locator arm 220 do not interfere with the reciprocating motion of the grippers 30,32 along the drawing tower 20, nor do they come in contact with the suspended strand 55. In the preferred embodiment, pneumatic air cylinder 222 enables reciprocating movement of the ball slide 228 along stationary guide 226 as shown in FIG. 6.

When cutting the strand of material 55, the retractable ball slide 228 reciprocates in the direction toward the strand 55 indicated by arrow "B" in FIG. 7 to bring the overcenter linkage 214, and consequently the cutting blade 230 and locator arm 220 to the cutting position shown in FIG. 8. As the overcenter linkage 214 moves to the cutting position, the link arm 217 translates the movement of the ball slide 228 into pivotal movement of the locator arm 220. Locator arm 220 is provided with a support block having a V-shaped notch 223 which functions to engage the strand of material 55 to be cut as the arm is pivoted into the cutting position. The V-shaped notch also functions to support the strand on two sides of the strand 55 while it is being horizontally cut on a third side. This enables clean, broom-free cuts especially of multi-filament suture material, which tends to form a broom end when the strand is under tension and is cut by scissors, or, when the multi-filament strand is sliced and not properly supported.

The cutting blade 230 of cutter assembly 200 is fixedly mounted to reciprocating ball slide 228 at a slight angle relative thereto and in a plane parallel with that of the locator arm 220. In the preferred embodiment, a single action by the pneumatic air cylinder 222 will enable movement of the reciprocating ball slide 228 along stationary guide 226. This consequently enables pivoting of locator arm 220 from its retracted position (FIG. 7), so that V-shaped notch 223 engages the strand 55 at two sides thereof while a third side of the strand bears upon the cutting edge of blade 230 as the blade moves towards the supported strand 55 traversing the drawing axis thereof. Thus, the strand 55 is cut in a dwell moment of the locator arm after the locator arm 220 has pivoted in the direction toward the blade 230 to the cutting position shown in FIG. 8. The blade 230 slices the strand of material while the strand is held stationary by locator arm 220 by virtue of the angled orientation of the blade with respect to the axis of reciprocation illustrated in FIGS. 7 and 8. In the preferred embodiment, the slice ratio is 1:1 or greater, with the blade 230 angled at approximately 45 degrees relative to the axis of reciprocation, so that the strand 55 is cut an amount equivalent to the distance the blade 230 traverses the drawing axis.

Preparing a predetermined length of (suture) material for cutting and swaging is accomplished as follows:

First, the indefinite length strand of suture material 55 is manually threaded through eyelet 56, and about pulleys 35a, 35b, and 112. The first gripping means including right gripper 32 is actuated to the gripping position as illustrated in FIG. 5, so that the suture strand 55 will be gripped in the manner described above. Next, the gripper draws the material strand 55 to the top portion of the drawing tower as shown in FIG. 3. Then, operable under the control of the control system computer 80, the right servo motor 38 is enabled to drive the lead (right) gripper vertically along right rod 28 to a predetermined height, all the while carrying suture material 55 in the manner described above. As shown in FIG. 2(a), proximity sensor 70 is mounted at a position along the right side rail 24 to verify that the right gripper 32 has reached its desired position. Likewise, a proximity sensor (not shown) is mounted at the desired height along the left side rail 22 to verify that the left gripper 30 has reached its desired location. As shown in FIG. 2(a), proximity sensors 73, 74, and 75 are positioned vertically at different heights along the drawing tower 20 to additionally predetermine suture material lengths to be cut. Specifically, the locations of the proximity sensors 73, 74, and 75 sense the positioning of the tip and cut assembly 100 as controlled by handcrank 108 in order to notify the control system 80 to change the reciprocating travel of grippers 30, 32.

In the preferred embodiment shown in FIG. 3, the lead gripper (gripper 32) grips the suture material on the tipped portion slightly below its tipped end 58 to register the tipped end for positioning within the suture receiving opening of a precisely registered surgical needle (not shown) for swaging thereof. To accomplish this, the lead gripper servomotor (e.g., servomotor 38) first advances the lead gripper for a long stroke distance, which may range from 12 inches to 36 inches depending upon the desired length of said suture strand, but is 16.1 inches in the preferred embodiment. The long stroke moves gripper 32 from a position at the tip and cut carrier 100 to the position illustrated in FIG. 3. Simultaneously therewith, the other servomotor, e.g., servomotor 36, positions the bottom gripper, e.g., left gripper 30, along left rod 26 at a location preferably below the position of the cutter assembly 200 as shown in FIGS. 3 and 4. It is understood that the lead gripper is gripping the material 55 at all times during the long stroke, while the bottom gripper is in its open position and not gripping.

The next step, indicated in FIG. 1 as step 17, is to position the lead gripper 32 so that the tipped end 58 of the suture material is positioned within the suture receiving opening of a surgical needle for swaging thereof. To accomplish this, the lead gripper 32 must again advance the suture material 55 for a short stroke distance of about 1.9 inches in the preferred embodiment, so that the tipped end 58 will advance precisely into the suture receiving opening of the surgical needle for a subsequent swaging operation to take place.

It should be understood that in another embodiment of the invention this step may consist of handing off the tip of the material to a subsequent material handling device, e.g., connecting a length of wire to a wire harness, or the like.

As the tipped end 58 of the indefinite length suture strand is advanced during the short stroke distance prior to swaging, a heated tipped portion 78 of the material 55 that has been heated by tipping assembly 300, (explained hereinbelow), advances to a position slightly above the location of the left gripper 30 and adjacent the cutter assembly 200. Then, while the automatic swaging of the tipped end 58 to the surgical needle takes place at the top of the tower 20, the left gripper 30 (lower gripper) is actuated to grip the material 55 in the heated tipped portion 78, i.e., the portion of the suture material heated by tipping assembly 300 as shown in FIG. 4. Simultaneous with the engagement of left gripper 30, the right (lead) gripper 32 is actuated to release its grip on the suture material.

Figure 9:
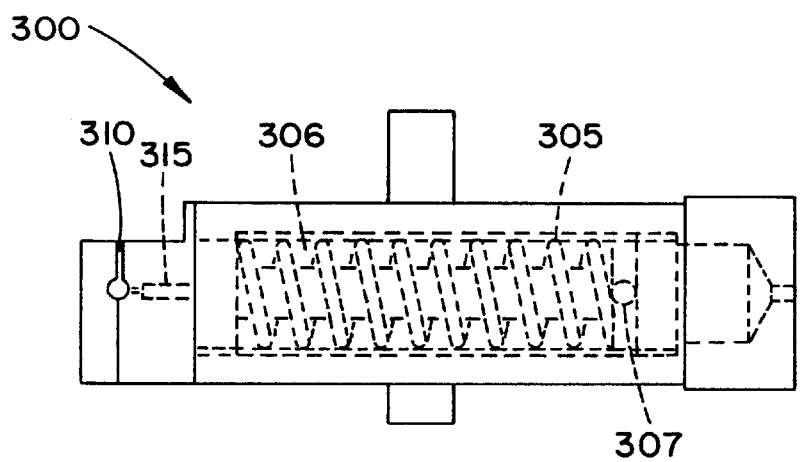
FIG. 9 is a detailed top view of the tipping assembly 300 for heating a portion of the suture material.

In the optional step indicated as step 16 in FIG. 1, the right or lead gripper is halted after the long stroke so that the portion of the suture material 55 may be heated (tipped) prior to cutting thereof. Heating the suture under tension and the subsequent cooling thereof will stiffen the material and aid in the positioning and subsequent swaging of the tip of the material within the confines of the suture receiving end of the surgical needle. The operation of the tipping assembly 300 will now be explained as follows:

As shown in FIG. 9, the tipping assembly 300 is essentially an oven comprising a heat exchanger unit 305 that heats the air in the heater cavity 306. When a pulse of incoming air is provided to the heat exchanger input 307, the heated air is displaced and it provides a pulse of heated air to a vertical cylindrical cavity 310 as shown in FIG. 4 and in the top view of FIG. 9. As shown in FIG. 4 the heated air is forced through horizontal orifice 315 for a predetermined duration so that the length of suture material 55 suspended in tension through vertical cavity 310 will be heated. The control system computer 80 controls the duration of the heat pulse so that the material is adequately heated and will have sufficient time to cool before the cutting operation. The temperature of the heated pulse may be suitably selected depending upon the surface area of the strand suspended through the vertical cavity 310. Preferably, the tipping assembly 300 is located at a position that is located slightly below the bottom or left gripper. As mentioned above, this is required so that when the suture material 55 is advanced the short stroke distance, the heated tipped portion 78 of material 55 will advance a corresponding distance so that it may be cut by cutter assembly 200. This ensures that the bottom gripper, e.g., left gripper 30, will grip the material having a new tipped end 58 for the next suture draw/insert cycle.

It should be understood that various other "tipping" technologies will work depending upon the type of suture material that is being processed. For instance, when VICRYL® and VICRYL®-like suture materials are used, tensioning of the strand, in addition to hot air application to a strand will enable the surface thereof to be melted and recast to form a stiffened tip. The application of tension in addition to a heated, grooved, die for forming the tip diameter of VICRYL® suture materials may also be used; however, the use of a die to form the tip diameter, requires closer control of the strand location to ensure that a tip gets into the die groove for every cycle. For wax-impregnated suture materials like silk, the application of tension only at predetermined locations, will form a stiffened portion of the suture strand at those locations. Another tipping method for use with braided suture materials, involves applying and penetrating the braid with a dilute resin material such as General Electric's VITEL® having a high solvent content, and quick drying the applied portions with hot air while maintaining tension of the suture strand materials to form a stiffened tip thereof.

After swaging of the surgical needle takes place and the left gripper 30 has secured the suture strand, the suture material 55 is cut by the cutting assembly 200 in the manner described above and as indicated in step 18 in FIG. 1. In the preferred embodiment shown in FIG. 4, a vacuum air flow is energized to pull the strand of material 55 toward the nylon screen 251 to more precisely locate the suture strand in the target zone of the cutter. After cutting of the indefinite length suture material 55 at the heated tipped portion 78, the tail end of the length of the cut suture material that had been swaged to the surgical needle is sucked into a large vacuum pipe 275, that is connected to a vacuum assembly 250 by vacuum hose 280 as shown in FIG. 4. The vacuum created in vacuum pipe 275 exerts a mild tension in the strand of material to keep the tail end 79 from entanglement or coming into contact with the machinery. However, it is mild enough to allow the strand to be pulled out of the pipe 275 as the armed needle and suture are handed off for further downstream processes.

FIG. 4 shows the left gripper 30 positioned slightly below the cutter assembly 200 so that the indefinite length strand will be gripped when the definite length swaged strand is cut. Thus, the left gripper now grips the suture material 55 having a tipped end 58 and it now becomes the lead gripper. The next cycle begins with the lead gripper vertically drawing the material 55 along the height of the drawing tower 20 for the long stroke to position the next strand to be cut for insertion within the surgical needle.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. An apparatus for cutting a flexible indefinite length suture strand to uniform lengths for subsequent threading and swaging to a surgical needle having a suture receiving opening formed therein, said apparatus comprising:
   (a) a drawing frame, said frame having at least one longitudinal member and defining a drawing axis parallel to said at least one longitudinal member;
   (b) feeding means for feeding said indefinite length suture strand to said drawing axis for drawing and cutting;
   (c) first and second gripping means for gripping said indefinite length suture strand and drawing it along said drawing axis, said first gripping means mounted for reciprocal movement on said at least one longitudinal member;
   (d) means for cutting said indefinite length suture strand;
   (e) first vacuum means for temporarily restraining the cut end of said suture strand after cutting; and
   (f) said second gripping means is mounted for reciprocal movement on said frame and is moved downwardly to a start position along said drawing axis located below said cutting means, while said first gripping means is drawing said indefinite length suture strand upwardly to a predetermined distance above said cutting means, and said first gripping means further advancing said indefinite length suture strand for insertion within said suture receiving end of said needle and cut to a predetermined length by said cutting means after said second gripping means has gripped said indefinite length suture strand at said start position.

2. An apparatus as claimed in claim 1, wherein said at least one longitudinal member further defines reciprocal guide means for at least one of said first and second gripping means.

3. An apparatus as claimed in claim 1 further comprising first and second drive motors operatively connected to said first and second gripping means to impart reciprocal movement to said first and second gripping means respectively.

4. An apparatus as claimed in claim 3 further comprising a control means for said first and second drive motors to draw said indefinite length suture strand to said predetermined distance beyond said cutting means.

5. An apparatus as claimed in claim 4 further comprising a moveable carrier mounted on said drawing frame for selective movement along said drawing axis, said movable carrier having said cutting means mounted thereon.

6. An apparatus as claimed in claim 5, wherein said control means comprises at least one sensor means for verifying the position of said moveable carrier.

7. An apparatus as claimed in claim 5 further including a treating means for heat treating a portion of said indefinite length strand for stiffening the same prior to cutting thereof, said treating means located at said start position.

8. An apparatus as claimed in claim 7 wherein said treating means is mounted on said movable carrier.

9. An apparatus as claimed in claim 1, wherein said feeding means further comprises means for tensioning said indefinite length suture strand during at least the drawing and cutting thereof.

10. An apparatus as claimed in claim 1, wherein each of said first and second gripping means further includes a pair of retractable gripping elements having a first engaged position and a second retracted position, wherein one of said first and second gripping means traverses the drawing axis on a draw stroke with its gripping elements engaging said indefinite length suture strand, and the other of said first and second gripping means reciprocates along the drawing axis with its gripping elements retracted to avoid mechanical interference with each other.

11. An apparatus as claimed in claim 1, wherein said apparatus further comprises a second vacuum means for proximate positioning of said indefinite length suture strand prior to cutting.

12. An apparatus according to claim 1, wherein said cutting means is a retractable cutter comprising:
   (a) a stationary guide means having a retractable cutting blade supported thereon for relative movement thereto, said guide means positioned in said apparatus to extend along a first axis;
   (b) an actuator mounted on said guide means for providing at least reciprocal movement to said cutting blade along a second axis;
   (c) a pivotal locating arm pivotally connected to said stationary guide means for positioning said indefinite length strand for cutting, said arm having a first end pivoting from a first retracted position to a second strand engaging position by movement of said actuator;
   (d) said cutting blade having at least reciprocal movement across said first axis, said cutting blade being operatively connected to said actuator to move from a first retracted position to a second cutting position;
   whereby a single action by said actuator will first position said strand with said pivotal arm and then cleanly cut said strand with said cutting blade.

13. An apparatus as claimed in claim 12, wherein said pivotal locating arm further comprises a support block for supporting said strand at a predetermined location on said first axis during the cutting of said strand.

14. An apparatus as claimed in claim 13, wherein an overcenter linkage is connected to said pivotal locating arm by a link arm for isolating motion from said actuator after said pivotal locating arm has engaged said strand.

15. An apparatus as claimed in claim 14 wherein said overcenter linkage translates a reciprocal movement from said actuator into pivotal movement for said locating arm.

16. An apparatus as claimed in claim 15 wherein said stationary guide means is spaced from said drawing axis by the effective length of said pivotal locating arm.

17. An apparatus as claimed in claim 14, wherein said overcenter linkage further comprises link means including a first link arm fixedly mounted on said actuator and a second link arm connecting said first link arm and said pivotal locating arm.

18. An apparatus as claimed in claim 13, wherein said means for cutting further comprises a blade holder fixedly mounted on said actuator and clampingly supporting said cutting blade during reciprocal motion of the actuator.

19. An apparatus as claimed in claim 18, wherein said cutting blade is angled with respect to said second axis to cut said strand with a slicing movement when said blade traverses said first axis.

20. An apparatus as claimed in claim 19, wherein said cutting blade and said pivotal locating arm are both retracted rearwardly of said stationary guide when said pivotal locating arm is in its first retracted position.

21. An apparatus as claimed in claim 12 wherein said first axis and said second axis are transverse to one another without intersection of each other.

22. An apparatus as claimed in claim 12 wherein said actuator is reciprocatably movable relative to said stationary guide.

23. An apparatus for cutting an indefinite length suture strand to uniform lengths for subsequent threading and swaging to a surgical needle having a suture receiving opening formed therein, said apparatus comprising:

(a) a drawing frame, said frame having at least one longitudinal member;

(b) a moveable carrier mounted on said longitudinal member for reciprocal movement along a drawing axis defined parallel to said at least one longitudinal member;

(c) means for feeding said indefinite length suture strand to said drawing axis for drawing and cutting; said feeding means comprising means for tensioning said indefinite length suture strand during at least the drawing and cutting thereof; said apparatus further having a treating means for heat treating a portion of said indefinite length strand for stiffening the same prior to cutting of said strand;

(d) at least one gripping means for gripping said indefinite length suture strand and drawing it along said drawing axis, said at least one gripping means mounted for reciprocal movement on said at least one longitudinal member;

(e) means for cutting said indefinite length suture strand, said cutting means being mounted on said moveable carrier;

(f) said at least one gripping means drawing said indefinite length suture strand to a predetermined distance beyond said cutting means, said at least one gripping means further drawing said indefinite length suture strand for insertion within said suture receiving opening of said needle and cut to a predetermined length by said cutting means.

24. An apparatus as claimed in claim 23, wherein said at least one longitudinal member further defines reciprocal guide means for said gripping means.

25. An apparatus as claimed in claim 23 further comprising at least one drive motor, said at least one drive motor including means connected thereto for imparting reciprocal movement to said gripping means.

26. An apparatus as claimed in claim 25 further comprising a control means for said drive motor to draw said suture strand to said predetermined distance beyond said cutting means.

27. An apparatus as claimed in claim 26, wherein said control means includes at least one sensor means for verifying the position of said moveable carrier.

28. An apparatus as claimed in claim 23 wherein said treating means is mounted on said moveable carrier.

29. An apparatus as claimed in claim 23, wherein said gripping means further includes retractable gripping elements having a first engaged position and a second retracted position, wherein said gripping means traverses said drawing axis on a draw stroke with said retractable gripping elements engaging said indefinite length suture strand.

30. An apparatus as claimed in claim 23 further including a first vacuum means for temporarily restraining a cut end of said suture strand after cutting thereof.

31. An apparatus as claimed in claim 30, wherein said apparatus further comprises a second vacuum means mounted on said moveable carrier for proximate positioning of said indefinite length suture strand prior to cutting.

32. An apparatus as claimed in claim 23, wherein said cutting means further includes a cutting blade and a support means for supporting the indefinite length suture strand during cutting thereof.

33. An apparatus for cutting an indefinite length suture strand to uniform lengths for subsequent threading and swaging to a surgical needle having a suture receiving opening formed therein, said apparatus comprising:

(a) a drawing frame, said frame having at least one longitudinal member and defining a drawing axis parallel to said longitudinal member;

(b) means for feeding said flexible indefinite length suture strand to said drawing axis for drawing and cutting, said feeding means comprising means for tensioning said indefinite length suture strand during at least the drawing and cutting thereof;

(c) first and second gripping means for gripping said indefinite length strand and drawing it along said drawing axis, said first gripping means mounted for reciprocal movement on said at least one longitudinal member;

(d) means for cutting said indefinite length suture strand;

(e) said second gripping means is mounted for reciprocal movement on said frame and is moved downwardly to a start position along said drawing axis to below said cutting means, while said first gripping means is drawing said suture strand upwardly for a long stroke terminating at a predetermined distance above said cutting means; and (f) treating means for treating a portion of said indefinite length suture strand at said start position after said first gripping means has advanced for said long stroke, said treating means providing heat to a portion of said indefinite length suture strand while under tension;

said first gripping means further drawing said indefinite length suture strand a short stroke distance to insert a free end thereof into said suture receiving opening of said needle, said indefinite length suture strand being additionally cut to a predetermined length by said cutting means after said second gripping means has gripped said indefinite length suture strand at said treated portion thereof.

* * * * *